US010531858B2

(12) United States Patent
Lachaine et al.

(10) Patent No.: US 10,531,858 B2
(45) Date of Patent: Jan. 14, 2020

(54) METHODS AND SYSTEMS FOR GUIDING THE ACQUISITION OF ULTRASOUND IMAGES

(75) Inventors: Martin Lachaine, Montreal (CA); Tony Falco, La Prairie (CA)

(73) Assignee: Elekta, LTD, Montreal, Quebec (CA)

( * ) Notice: Subject to any disclaimer, the term of this patent is extended or adjusted under 35 U.S.C. 154(b) by 908 days.

(21) Appl. No.: 12/176,774

(22) Filed: Jul. 21, 2008

(65) Prior Publication Data
US 2009/0024030 A1   Jan. 22, 2009

Related U.S. Application Data

(60) Provisional application No. 60/951,001, filed on Jul. 20, 2007.

(51) Int. Cl.
*A61B 8/08* (2006.01)
*A61B 8/00* (2006.01)
*A61B 8/14* (2006.01)

(52) U.S. Cl.
CPC .............. *A61B 8/0825* (2013.01); *A61B 8/14* (2013.01); *A61B 8/4245* (2013.01); *A61B 8/4416* (2013.01); *A61B 8/4218* (2013.01)

(58) Field of Classification Search
CPC ....... A61B 8/13; A61B 8/0825; A61B 8/4218; A61B 8/14; A61B 8/4245; A61B 8/4416
USPC ............................ 600/437; 382/128; 601/1, 2
See application file for complete search history.

(56) References Cited

U.S. PATENT DOCUMENTS

| | | | |
|---|---|---|---|
| 3,082,322 A | 3/1963 | Koerner et al. | |
| 3,777,124 A | 12/1973 | Pavkovich | |
| 3,987,281 A | 10/1976 | Hodes | |
| 3,991,310 A | 11/1976 | Morrison | |
| 4,118,631 A | 10/1978 | Froggatt | |
| 4,618,978 A | 10/1986 | Cosman | |
| 4,882,741 A | 11/1989 | Brown et al. | |

(Continued)

FOREIGN PATENT DOCUMENTS

| | | |
|---|---|---|
| CA | 2416887 | 2/2002 |
| CA | 2621741 A1 | 3/2007 |

(Continued)

OTHER PUBLICATIONS

Besl et al., *A Method for Registration of 3d Shapes*, IEEE Transactions on Pattern Analysis and Machine Intelligence 14(2):239-256 (1992).

(Continued)

*Primary Examiner* — Boniface N Nganga
(74) *Attorney, Agent, or Firm* — Schwegman Lundberg & Woessner, P.A.; Sanjay Agrawal

(57) ABSTRACT

A method of presenting a suggested path for an ultrasound probe along a patient's surface includes obtaining a three-dimensional, non-ultrasound image of the patient and an ultrasound image of the patient. A treatment area is defined within the within the three-dimensional, non-ultrasound image, and using the images, defining a scanning site contour of an anatomical structure of interest within the patient and an external contour of the patient's surface. A preferred path of the ultrasound scan is projected onto the external contour such that an operator can reproduce the ultrasound scan without knowledge of the anatomical structure of interest.

16 Claims, 5 Drawing Sheets

(56) References Cited

U.S. PATENT DOCUMENTS

| | | | |
|---|---|---|---|
| 4,923,459 A | 5/1990 | Nambu | |
| 4,943,990 A | 7/1990 | Schar | |
| 5,039,867 A | 8/1991 | Nishihara et al. | |
| 5,080,100 A | 1/1992 | Trotel | |
| 5,086,401 A | 2/1992 | Glassman et al. | |
| 5,099,846 A | 3/1992 | Hardy | |
| 5,107,839 A | 4/1992 | Houdek et al. | |
| 5,117,829 A | 6/1992 | Miller et al. | |
| 5,138,647 A | 8/1992 | Nguyen et al. | |
| 5,207,223 A | 5/1993 | Adler | |
| 5,222,499 A | 6/1993 | Allen et al. | |
| 5,233,990 A | 8/1993 | Barnea | |
| 5,291,889 A | 3/1994 | Kenet et al. | |
| 5,295,483 A | 3/1994 | Nowacki et al. | |
| 5,299,288 A | 3/1994 | Glassman et al. | |
| 5,301,674 A | 4/1994 | Erikson et al. | |
| 5,379,642 A | 1/1995 | Reckwerdt et al. | |
| 5,389,101 A | 2/1995 | Heilbrun et al. | |
| 5,391,139 A | 2/1995 | Edmundson | |
| 5,397,329 A | 3/1995 | Allen | |
| 5,408,101 A | 4/1995 | Wong | |
| 5,411,026 A | 5/1995 | Carol | |
| 5,438,991 A | 8/1995 | Yu et al. | |
| 5,442,675 A | 8/1995 | Swerdloff et al. | |
| 5,446,548 A | 8/1995 | Gerig et al. | |
| 5,447,154 A | 9/1995 | Cinquin et al. | |
| 5,483,961 A | 1/1996 | Kelly et al. | |
| 5,511,549 A | 4/1996 | Legg et al. | |
| 5,524,627 A * | 6/1996 | Passi | 600/445 |
| 5,531,227 A | 7/1996 | Schneider | |
| 5,531,520 A | 7/1996 | Grimson et al. | |
| 5,553,618 A | 9/1996 | Suzuki et al. | |
| 5,591,983 A | 1/1997 | Yao | |
| 5,603,318 A | 2/1997 | Heilbrun et al. | |
| 5,609,485 A * | 3/1997 | Bergman et al. | 434/262 |
| 5,645,066 A * | 7/1997 | Gandini et al. | 600/443 |
| 5,673,300 A | 9/1997 | Reckwerdt et al. | |
| 5,690,108 A | 11/1997 | Chakeres | |
| 5,715,166 A | 2/1998 | Besl et al. | |
| 5,734,384 A | 3/1998 | Yanof et al. | |
| 5,740,225 A | 4/1998 | Nabatame | |
| 5,754,623 A * | 5/1998 | Seki | 378/65 |
| 5,757,881 A | 5/1998 | Hughes | |
| 5,778,043 A | 7/1998 | Cosman | |
| 5,810,007 A * | 9/1998 | Holupka et al. | 600/439 |
| 5,836,954 A | 11/1998 | Heilbrun et al. | |
| 5,851,183 A | 12/1998 | Bucholz | |
| 5,859,891 A | 1/1999 | Hibbard | |
| 5,871,445 A | 2/1999 | Bucholz | |
| 5,952,577 A * | 9/1999 | Passi | 73/618 |
| 5,991,703 A | 11/1999 | Kase et al. | |
| 6,019,724 A | 2/2000 | Gronningsaeter et al. | |
| 6,038,283 A | 3/2000 | Carol et al. | |
| 6,094,508 A | 7/2000 | Acharya et al. | |
| 6,106,470 A | 8/2000 | Geiser et al. | |
| 6,112,341 A | 9/2000 | Moreland | |
| 6,117,081 A | 9/2000 | Jago et al. | |
| 6,118,848 A | 9/2000 | Reiffel | |
| 6,119,033 A | 9/2000 | Spigelman et al. | |
| 6,122,341 A | 9/2000 | Butler et al. | |
| 6,129,670 A | 10/2000 | Burdette et al. | |
| 6,138,495 A | 10/2000 | Paltieli et al. | |
| 6,144,875 A | 11/2000 | Schweikard et al. | |
| 6,146,390 A | 11/2000 | Heilbrun et al. | |
| 6,198,957 B1 | 3/2001 | Green | |
| 6,208,883 B1 | 3/2001 | Holupka et al. | |
| 6,259,943 B1 | 7/2001 | Cosman et al. | |
| 6,269,143 B1 | 7/2001 | Tachibana | |
| 6,285,805 B1 | 9/2001 | Gueziec | |
| 6,292,578 B1 | 9/2001 | Kalvin | |
| 6,307,914 B1 | 10/2001 | Kunieda et al. | |
| 6,314,310 B1 | 11/2001 | Ben-Haim et al. | |
| 6,325,758 B1 | 12/2001 | Carol et al. | |
| 6,345,114 B1 | 2/2002 | Mackie et al. | |
| 6,359,959 B1 | 3/2002 | Butler et al. | |
| 6,366,798 B2 | 4/2002 | Green | |
| 6,385,286 B1 | 5/2002 | Fitchard et al. | |
| 6,385,288 B1 | 5/2002 | Kanematsu | |
| 6,390,982 B1 | 5/2002 | Bova et al. | |
| 6,405,072 B1 | 6/2002 | Cosman | |
| 6,423,009 B1 | 7/2002 | Downey et al. | |
| 6,438,202 B1 | 8/2002 | Olivera et al. | |
| 6,459,769 B1 | 10/2002 | Cosman | |
| 6,470,207 B1 * | 10/2002 | Simon | A61B 6/463 378/207 |
| 6,491,702 B2 | 12/2002 | Heilbrun et al. | |
| 6,511,430 B1 | 1/2003 | Sherar et al. | |
| 6,516,046 B1 | 2/2003 | Frohlich et al. | |
| 6,535,574 B1 | 3/2003 | Collins et al. | |
| 6,546,073 B1 | 4/2003 | Lee | |
| 6,553,152 B1 | 4/2003 | Miller et al. | |
| 6,560,311 B1 | 5/2003 | Shepard et al. | |
| 6,567,684 B1 | 5/2003 | Chenevert et al. | |
| 6,585,651 B2 | 7/2003 | Nolte et al. | |
| 6,591,127 B1 | 7/2003 | McKinnon | |
| 6,600,810 B1 | 7/2003 | Hughes | |
| 6,621,889 B1 | 9/2003 | Mostafavi | |
| 6,628,983 B1 | 9/2003 | Gagnon | |
| 6,631,284 B2 | 10/2003 | Nutt et al. | |
| 6,636,622 B2 | 10/2003 | Mackie et al. | |
| 6,641,539 B2 | 11/2003 | Hirooka et al. | |
| 6,661,870 B2 | 12/2003 | Kapatoes et al. | |
| 6,662,036 B2 | 12/2003 | Cosman | |
| 6,669,635 B2 | 12/2003 | Kessman et al. | |
| 6,683,985 B1 | 1/2004 | Kase et al. | |
| 6,690,965 B1 | 2/2004 | Riaziat et al. | |
| 6,714,627 B1 | 3/2004 | Brown et al. | |
| 6,725,079 B2 | 4/2004 | Zuk et al. | |
| 6,728,424 B1 | 4/2004 | Zhu et al. | |
| 6,731,970 B2 | 5/2004 | Schlossbauer et al. | |
| 6,750,873 B1 | 6/2004 | Bernardini et al. | |
| 6,754,374 B1 | 6/2004 | Miller et al. | |
| 6,785,409 B1 | 8/2004 | Suri | |
| 6,804,548 B2 | 10/2004 | Takahashi et al. | |
| 6,842,502 B2 | 1/2005 | Jaffray et al. | |
| 6,914,959 B2 | 7/2005 | Bailey et al. | |
| 6,915,008 B2 | 7/2005 | Barman et al. | |
| 6,968,224 B2 | 11/2005 | Kessman et al. | |
| 6,980,679 B2 | 12/2005 | Jeung et al. | |
| 7,092,109 B2 | 8/2006 | Satoh et al. | |
| 7,095,823 B2 | 8/2006 | Topolnjak et al. | |
| 7,260,426 B2 | 8/2007 | Schweikard et al. | |
| 7,333,644 B2 | 2/2008 | Jerebko et al. | |
| 7,343,030 B2 | 3/2008 | Sawyer | |
| 7,430,321 B2 | 9/2008 | Okada et al. | |
| 7,438,685 B2 | 10/2008 | Burdette et al. | |
| 7,535,411 B2 | 5/2009 | Falco | |
| 7,613,501 B2 | 11/2009 | Scherch | |
| 7,634,304 B2 | 12/2009 | Falco et al. | |
| 7,662,097 B2 | 2/2010 | Falco et al. | |
| 7,672,705 B2 | 3/2010 | Lachaine et al. | |
| 7,729,744 B2 | 6/2010 | Falco et al. | |
| 7,801,349 B2 | 9/2010 | Wang et al. | |
| 8,042,209 B2 | 10/2011 | D'Souza et al. | |
| 8,160,676 B2 * | 4/2012 | Gielen et al. | 600/427 |
| 8,232,535 B2 | 7/2012 | Olivera et al. | |
| 2001/0035871 A1 | 11/2001 | Bieger et al. | |
| 2001/0049475 A1 | 12/2001 | Bucholz et al. | |
| 2002/0018588 A1 | 2/2002 | Kusch | |
| 2002/0065461 A1 | 5/2002 | Cosman | |
| 2002/0082494 A1 | 6/2002 | Balloni et al. | |
| 2002/0087101 A1 | 7/2002 | Barrick et al. | |
| 2002/0122530 A1 | 9/2002 | Erbel et al. | |
| 2002/0156375 A1 | 10/2002 | Kessman et al. | |
| 2002/0176541 A1 | 11/2002 | Schubert et al. | |
| 2002/0183610 A1 | 12/2002 | Foley et al. | |
| 2002/0188194 A1 | 12/2002 | Cosman | |
| 2003/0018232 A1 | 1/2003 | Elliott et al. | |
| 2003/0028401 A1 | 2/2003 | Kaufman et al. | |
| 2003/0112922 A1 | 6/2003 | Burdette et al. | |
| 2003/0144813 A1 | 7/2003 | Takemoto et al. | |
| 2003/0153825 A1 | 8/2003 | Mooradian et al. | |
| 2003/0182072 A1 | 9/2003 | Satoh et al. | |
| 2003/0220557 A1 * | 11/2003 | Cleary et al. | 600/409 |

(56) References Cited

U.S. PATENT DOCUMENTS

| | | |
|---|---|---|
| 2003/0231790 A1 | 12/2003 | Bottema |
| 2004/0015075 A1 | 1/2004 | Kimchy et al. |
| 2004/0015176 A1 | 1/2004 | Cosman |
| 2004/0034301 A1 | 2/2004 | Falco |
| 2004/0092815 A1 | 5/2004 | Schweikard et al. |
| 2004/0146137 A1 | 7/2004 | Bruder et al. |
| 2004/0176925 A1 | 9/2004 | Satoh et al. |
| 2004/0184646 A1 | 9/2004 | Oosawa |
| 2004/0252870 A1 | 12/2004 | Reeves et al. |
| 2004/0260142 A1 | 12/2004 | Lovoi |
| 2005/0020917 A1 | 1/2005 | Scherch |
| 2005/0180544 A1 | 8/2005 | Sauer et al. |
| 2005/0251029 A1 | 11/2005 | Khamene et al. |
| 2006/0020195 A1 | 1/2006 | Falco et al. |
| 2006/0074292 A1 | 4/2006 | Thomson et al. |
| 2006/0093205 A1 | 5/2006 | Bryll et al. |
| 2006/0120608 A1 | 6/2006 | Luo et al. |
| 2006/0241443 A1 | 10/2006 | Whitmore et al. |
| 2006/0285641 A1 | 12/2006 | Scherch |
| 2006/0293583 A1 | 12/2006 | Saracen et al. |
| 2007/0010743 A1* | 1/2007 | Arai .................. A61B 8/13 600/443 |
| 2007/0015991 A1 | 1/2007 | Fu et al. |
| 2007/0038058 A1 | 2/2007 | West et al. |
| 2007/0055090 A1 | 3/2007 | Neustadter et al. |
| 2008/0021317 A1* | 1/2008 | Sumanaweera ...... A61B 8/4218 600/437 |
| 2008/0039713 A1 | 2/2008 | Thomson et al. |
| 2008/0064953 A1 | 3/2008 | Falco et al. |
| 2008/0200794 A1* | 8/2008 | Teichman et al. ............ 600/407 |
| 2008/0219405 A1 | 9/2008 | Falco et al. |
| 2008/0292194 A1 | 11/2008 | Schmidt et al. |
| 2009/0003523 A1 | 1/2009 | Raanes et al. |
| 2009/0093716 A1 | 4/2009 | Deischinger et al. |
| 2009/0110145 A1 | 4/2009 | Lu et al. |
| 2011/0069815 A1 | 3/2011 | Nord et al. |

FOREIGN PATENT DOCUMENTS

| | | |
|---|---|---|
| EP | 0647457 | 4/1995 |
| EP | 951697 A1 | 10/1999 |
| EP | 1304960 | 5/2003 |
| EP | 1426806 A2 | 6/2004 |
| EP | 1757228 A1 | 2/2007 |
| FR | 2778574 | 11/1999 |
| JP | 2006000220 A | 1/2006 |
| WO | WO-19992074 A1 | 1/1999 |
| WO | WO-99/06644 | 2/1999 |
| WO | WO-99/26534 | 6/1999 |
| WO | WO-99/27839 | 6/1999 |
| WO | WO-200105316 A1 | 1/2001 |
| WO | WO-200209588 A1 | 2/2002 |
| WO | WO-2003/039370 A1 | 5/2003 |
| WO | WO-2003/076003 | 9/2003 |
| WO | WO-2006051523 A2 | 5/2006 |

OTHER PUBLICATIONS

Booth, *Modelling the impact of treatment uncertainties in radiotherapy*, University of Adelaide, Mar. 2002), Section 2.4 (<http://thesis.library.adelaide.edu.au/uploads/approved/adt-SUA20020816.175301/public/03chapter2.pdf>.

Brujic et al., *Analysis of Free-Form Surface Registration*, International Conference on Image Processing, pp. 393-396 (1996).

Cuisenaire, O., http://www.tele.ucl.ac.be/PEOPLE/OC/these/node74.html, Posted Oct. 5, 1999, Downloaded from the Internet on Aug. 10, 2004.

Cuisenaire, O., http://www.tele.ucl.ac.be/PEOPLE/OC/these/node75.html, Posted Oct. 5, 1999, Downloaded from the Internet on Aug. 10, 2004.

Cuisenaire, O., http://www.tele.ucl.ac.be/PEOPLE/OC/these/node12.html, Posted Oct. 5, 1999, Downloaded from the Internet on Aug. 10, 2004.

Dubois et al. Intraobserver and Interobserver Variability of MR Imaging- and CT-derived Prostate Volumes after Transperineal Interstitial Permanent Prostate Brachytherapy, Radiology. 207(3):785-9 (1998).

Eggert et al., *Simultaneous Registration of Multiple Range Views for Reverse Engineering*, International Conference of Pattern Recognition, pp. 243-247 (1996).

Hanks, et al. , Three Dimensional Conformal External Beam Treatment of Prostate Cancer <http://prostate-help.org/download/pilgrim/10rad.pdf>.

Hanks et al., Clinical and Biochemical Evidence of Control of Prostate Cancer at 5 Years After External Beam Radiation, The Journal of Urology, vol. 154, 456-459 (1995).

Haralick et al., *Pose Estimation From Corresponding Data Point*, IEEE Transactions on Systems, Man, and Cybernetics, 19(6):1426-1446 (1989).

Hua et al., Development of a Semi-Automatic Alignment Tool for Accelerated Localization of the Prostate, Int. J. Radiation Oncology Biol. Phys., 55(3):811-823 (2003).

Jiang et al., *A New Approach to 3-d Registration of Multimodality Medical Images by Surface Matching*, SPIE vol. 1808 Visualization in Biomedical Computing,, pp. 196-213 (1992).

Krempien et al., Daily patient set-up control in radiation therapy by coded light projection, 3 pages.

Michalski et al., *Three-Dimensional Conformal Radiation Therapy (3DCRT) for Prostate Cancer*, Radiation Oncology Center, Mallinckrodt Institute of Radiology, Washington University Medical Center, St. Louis, Missouri (1996) <http://www.phoenix5.org/Infolink/Michalski/#3>.

Paskalev et al., Daily Target Localization for Prostate Patients based on 3-D Image Correlation, Phys. Med. Biol., vol. 49, pp. 931-939 (2004).

Pennec et al,. A Framework for Uncertainty and Validation of 3-D Registration Methods Based on Points and Frames, International Journal of Computer Vision 25(3), 203-229 (1997).

Pito, *A Registration Aid*, International Conference on Recent Advanced in 3D Digital Imaging and Modelling, pp. 85-92 (1997).

Pollack et al., Conventional vs. Conformal Radiotherapy for Prostate Cancer: Preliminary Results of Dosimetry and Acute Toxicity, Int. J. Radiation Oncology Biol. Phys., 34(3):555-564.

Robb, *Three-Dimensional Visualization in Medicine and Biology*. Book Chapter in: Handbook of Medical Imaging: Processing and Analysis, ed. Isaac N. Bankman, Academic Press, San Diego, CA, Chapter 42, pp. 685-71 (2000).

Robinson, *Advances in Multi-Modal Data Analysis: The ANALYZE Software Environment*, <http://www.ii.metu.edu.tr/~med-ii/makaleler/analyze_sw_enve.pdf>, 5 pages. Downloaded on Aug. 10, 2004.

Soffen E.M. et al. Conformal static field radiation therapy treatment of early prostate cancer versus non-conformal techniques: A reduction in acute morbidity. Int J Radiat Oncol Biol Phys, 24: 485-488 (1992).

Thayananthan, A. et al., <http://mi.eng.cam.ac.uk/~bdrs2/papers/thayananthan_cvpr03.pdf>, pp. 1-8. Downloaded from the Internet on Aug. 10, 2004.

Tome et al., Commissioning and Quality Assurance of an Optically Guided Three-dimensional Ultrasound Target Localization System for Radiotherapy, Med. Phys., 29(8):1781-1788 (2002).

Zhang, Iterative Point Matching for Registration of Free-Form Curves and Surfaces, International Journal of Computer Vision, 13(2):119-152 (1994).

<http://www.ucsf.edu/jpouliot/Course/chapter5.htm>.

<http://www.acmp.org/meetings/hershey_2001/highlights/benedict.pdf>.

<http://www.ucsf.edu/jpouliot/Course/Lesson22.htm>.

<http://www.gemedicalsystems.com/patient/see_treat/positioning.html>.

<http://www.emoryradiationoncology.org/high-technology.htm>.

<http://www.varian.com/pinf/imr000c.html>.

<http://www.ucsf.edu/jpouliot/Course/conformal_radiation_therapy.htm>.

Written Opinion of the International Search report for PCT/CA2005/001105 dated Oct. 27, 2005.

(56) References Cited

OTHER PUBLICATIONS

International Search Report for PCT/CA2005/01105 dated Oct. 27, 2005.
International Search Report for PCT/CA2005/001106 dated Nov. 15, 2005.
Written Opinion for PCT/CA2005/001106 dated Nov. 15, 2005.
International Preliminary Report on Patentability for International Application No. PCT/CA2005/001106 dated Jan. 23, 2007.
Written Opinion of the International Searching Authority for International Application No. PCT/CA2005/001106 dated Oct. 25, 2005.
International Search Report for PCT/CA2007/001626 dated Jan. 3, 2008 (4 pages).
Written Opinion of the International Searching Authority for PCT/CA2007/001626 dated Dec. 21, 2007 (7 pages).
International Preliminary Report on Patentability for PCT/CA2005/001428 dated Oct. 3, 2007 (1 page).
Written Opinion of the International Searching Authority for PCT/CA2005/001428 dated Nov. 8, 2005 (6 pages).
International Search Report for PCT/CA2007/000898 dated Jul. 12, 2007 (3 pages).
Written Opinion of the International Searching Authority for PCT/CA2007/000898 dated Jul. 23, 2007 (6 pages).
International Search Report for PCT/CA2006/001289 dated Oct. 30, 2006 (3 pages).
Written Opinion of the International Searching Authority for PCT/CA2006/001289 dated Oct. 30, 2006 (6 pages).
Written Opinion of the International Searching Authority for PCT/CA2006/001461 dated Dec. 8, 2006 (5 pages).
International Search Report for PCT/CA2006/001461 dated Nov. 30, 2006 (5 pages).
International Search Report for PCT/CA2008/001338 dated Oct. 16, 2008, (2 pages).
Written Opinion of the International Searching Authority for PCT/CA2008/001338 dated Oct. 16, 2008 (6 pages).
Search Report for European Application No. 08783253.1 dated Dec. 30, 2011 (8 pages).
Holupka, et al., (1996), "Ultrasound Image Fusion for External Beam Radiotherapy for Prostate Cancer," J. Radiation Oncology Biol. Phys., vol. 35, No. 5, pp. 975-984.
International Search Report and Written Opinion for International Application No. PCT/CA2010/002008 dated May 2, 2012, 7 pages.
European Search Report for PCT/CA2007/001626 dated Nov. 5, 2010 (6 pages).
Brigger, et al., "B-Spline Snakes: A Flexible Tool for Parametric Contour Detection," IEEE Transactions on Image Processing, vol. 9, No. 9, Sep. 2000, pp. 1484-1496.
U.S. Appl. No. 13/083,680, filed Apr. 11, 2011 by Luzzara.
U.S. Appl. No. 13/166,957, filed Jun. 23, 2011 by Remeijer et al.
U.S. Appl. No. 13/179,818, filed Jul. 11, 2011 by Jarliden et al.
U.S. Appl. No. 12/479,126, filed Jun. 5, 2009 by Falco, et al.
U.S. Appl. No. 12/769,272, filed Apr. 28, 2010 by Falco et al.
U.S. Appl. No. 12/647,852, filed Dec. 28, 2009 by Falco et al.
U.S. Appl. No. 11/516,722, filed Sep. 6, 2006 by Falco et al.
U.S. Appl. No. 11/313,236, filed Dec. 20, 2005 by Lathuiliere et al.
U.S. Appl. No. 11/804,594, filed May 18, 2007 by Koptenko et al.
U.S. Appl. No. 11/852,492, filed Sep. 10, 2007 by Falco et al.
U.S. Appl. No. 12/186,801, filed Aug. 6, 2008 by Lachaine et al.
U.S. Appl. No. 12/176,785, filed Jul. 21, 2008 by Falco et al.
U.S. Appl. No. 12/473,506, filed May 28, 2009 by Dussault et al.
U.S. Appl. No. 12/831,546, filed Jul. 7, 2010 by Lachaine et al.
U.S. Appl. No. 12/956,991, filed Nov. 30, 2010 by Lachaine et al.
U.S. Appl. No. 13/239,795, filed Sep. 22, 2011 by Lachaine et al.
Aoki, Y. et al. An Integrated Radiotherapy Treatment System and its Clinical Application, Radiation Medicine, vol. 5, No. 4, pp. 131-141, 1987.
Barratt, Dean C., "Accuracy of an Electromagnetic Three-Dimensional Ultrasound System for Carotid Artery Imaging" from Ultrasound in Medicine and Biology, vol. 27, No. 10, 2001, pp. 1421-1425.
Bijhold, J. et al. Fast evaluation of patient set-up during radiotherapy by aligning features in portal and simulator images, Phys. Med. Biol., 1999, vol. 36, No. 12, pp. 1665-1679.
Bijhold, J. Three-dimensional verification of patient placement during radiotherapy using portal images, Med. Phys. 20 (2), Pt. 1, Mar./Apr. 1993. pp. 347-356.
Boctor, et al., A Rapid Calibration Method for Registration and 3D Tracking of Ultrasound Images Using Spatial Localizer, Proceedings of the SPIE (2003).
Boyer, A. A review of electronic portal imaging devices (EPIDs), Med. Phys. 19 (1), Jan./Feb. 1992 pp. 1-.
Brunie L. et al. Pre-and intra-irradiation multimodal image registration: principles and first experiments, Radiotherapy and Oncology 29 (1993) pp. 244-252.
Christensen G. E., Inverse consistent registration with object boundary constraints, Biomedical Imaging: Macro to Nano, 2004, IEEE International Symposium on Arlington, VA, USA Apr. 15-18, 2004, Piscataway, NJ, USA, IEEE (4 pages).
Claim Chart for Claim 10 of U.S. Pat. No. 5,447,154.
Cuadra, M.B. et al., Atlas-based Segmentation of pathological MR brain images using a model of lesion growth; Medical Imaging IEEE Transactions on, vol. 23, No. 10, pp. 1301-1314, Oct. 2004.
Czamota G.J. et al. Ultrasound imaging of apoptosis: high-resolution non-invasive monitoring of programmed cell death in vitro, in situ and in vivo, British Journal of Cancer (1999) 81(3), pp. 520-527.
International Search Report and Written Opinion for PCT/CA2009/000750, dated Sep. 18, 2009 (8 pages).
International Search Report for PCT/CA2005/001428 dated Nov. 16, 2005.
Le Verre, C. et al. Intensity-Based Registration of Portal Images for Patient Positioning in Radiotherapy.
Leszczynski K W et al., "An Image Registration scheme applied to verification of radiation therapy" British Journal of Radiology British Inst. Radiol UK [Online] vol. 71, No. 844, Apr. 1998 (Apr. 1998), ISSN: 0007-1285, retrieved from the Internet: url:http://bjr.birjournals.org/cgi/reprint/71/844/413.pdf. [retrieved on Nov. 10, 2009].
Lizzi, Frederic, et al., "Ultrasonic Spectrum Analysis of Tissue Assays and Therapy Evaluation," International Journal of Imaging Systems and Technology, Wiley and Sons, New York, vol. 8, No. 1, (Jan. 1, 1997), pp. 3-10.
Maurer C R et al., Registration of 3-D Images Using Weighted Geometrical Features, IEEE Transactions on Medical Imaging, IEEE Service Center, Piscataway, NJ, US vol. 15, No. 6, Dec. 1, 1996 (14 pages).
Meertens, H. et al. A method for the measurement of field placement errors in digital portal images, Phys. Med. Biol., 1990, vol. 35, No. 3, pp. 299-323.
Mencarelli, et al., "A Dosimetric Method to derive optimal couch corrections in the presence of anatomical deformations for H & N cancer," abstract, 2011, 2 pages.
Nagel, et al., "Online dose-guided setup correction protocol for hypo fractionated lung radiotherapy," abstract, 2009, 1 page.
Reinstein, L. et al. Radiotherapy Portal Imaging Quality, Report of AAPM Task Group No. 28, American Association of Physicists in Medicine by the American Institute of Physics, New York, 1988.
Search Report for European Patent Application No. 06790638.8, dated Apr. 23, 2010 (7 pages).
Simpson, R.G. et al. A 4-MV CT scanner for radiation therapy: The prototype system. Med. Phys. 9(4), Jul./Aug. 1982, pp. 574-579.
Supplementary European Search Report dated Oct. 25, 2010 (5 pages).
Supplementary European Search Report dated Oct. 30, 2008 for European Patent Application No. 05788508.9/PCT/CA2005001428.
Supplementary European Search Report for PCT/CA2005001106_RNM-003PC_dated Nov. 10, 2009, 6 pages.
Supplementary European Search Report, for PCT Application No. PCT/CA2005001135, dated Feb. 27, 2009 (12 pages).
Supplementary Partial European Search Report for EP Application No. 5763463, dated Nov. 30, 2009, 7 pages.

(56) References Cited

OTHER PUBLICATIONS

Swindell, W. et al. Computed tomography with a linear accelerator with radiotheraphy applications, Med. Phys. 10(4), Jul./Aug. 1983, pp. 416-420.

Troccaz, J. et al. Conformal external radiotherapy of prostatic carcinoma: requirements and experimental results, Radiotherapy and Oncology 29 (1993) pp. 176-183.

Troccaz., J et al. Patient Setup Optimization for External Conformal Radiotherapy, Journal of Image Guided Surgery, 1, pp. 113-120 (1995).

Van de Geijn, J. et al. A Graticule for Evaluation of Megavolt X Ray Port Films, Radiation Oncology Biology Physics, Nov. 1982, vol. 8, No. 11 pp. 1999-2000.

Zitova, B. et al., Image Registration Methods: A survey, Image and Vision Computing, Elsevier, Guildford, GB, vol. 21, No. 11, Oct. 1, 2003 (24 pages).

\* cited by examiner

METHODS AND SYSTEMS FOR GUIDING THE ACQUISITION OF ULTRASOUND IMAGES

CROSS-REFERENCE TO RELATED APPLICATIONS

This application claims priority to and the benefit of, and incorporates herein by reference, in its entirety, provisional U.S. patent application Ser. No. 60/951,001, filed Jul. 20, 2007.

TECHNICAL FIELD

This invention relates to methods for guiding the acquisition of images of anatomical features, and more specifically, guiding the rapid acquisition of ultrasound images that encompass particular features of interest.

BACKGROUND INFORMATION

The use of ultrasound imaging systems requires advanced training and is most often performed by sonographers or physicians who have an intimate knowledge of the anatomy under study, as well as the expected appearance of anatomical features in an ultrasound image. For example, in order to pinpoint the correct probe positioning to acquire an image of a desired anatomical structure (e.g., an organ, lesion or tumor), an operator must coordinate moving the ultrasound probe to the correct location on the anatomy while simultaneously interpreting the resulting images on a display.

Ultrasound has recently been introduced into the field of image-guided radiotherapy (IGRT) in which anatomical structures of interest are imaged immediately prior to a radiotherapy treatment session in order to correctly align the structures of interest to therapeutic radiation beams. Heretofore, ultrasound has most commonly been used for prostate IGRT in which a three-dimensional ultrasound scan (or, in some cases, multiple two-dimensional scans having known three-dimensional positions in space) of the prostate are acquired. These images are used to align the prostate to reproduce a previously-defined treatment plan accounting for daily prostate motion, growth, etc. One challenge is that radiation therapists, who typically have no ultrasound training, are expected to acquire the ultrasound images during the radiation delivery phase of treatment. Because the prostate is always in approximately the same location relative to the bladder, finding it using ultrasound can be relatively easy given some training for the therapists.

However, there are other potential applications for ultrasound-based IGRT in which an operator cannot rely on a consistent location of the anatomical feature of interest, for example, guiding localized breast-cancer radiotherapy treatments in which the main structure of interest is typically a lumpectomy cavity (i.e. the original site of the surgically-removed tumor). While some cavities may be easily found using ultrasound, others can be more difficult to identify. Further, unlike the prostate, which is always in the same general area within the patient, the therapist does not know where to look for the cavity—it can be anywhere within the breast, and therefore requires significant time and experience to find.

As part of radiation therapy, a computed tomography (CT) scan of the area of interest is typically taken for planning purposes prior to the first treatment session. As described in U.S. patent application Ser. No. 10/343,336, entitled "Method and Apparatus for Lesion Localization, Definition and Verification" a three-dimensional ultrasound image may also be acquired immediately before or after acquiring the CT scan. This image is typically acquired by either a CT technologist, radiation therapist or radiation oncologist, who also may not have ultrasound experience, giving rise to the same issues as ultrasound-based IGRT.

Because time and trained operators are scarce in a radiotherapy department, finding an anatomical structure such as a lesion cavity using an ultrasound imaging system can be a limiting task in ultrasound-based IGRT of the breast. Other anatomical sites may share the same problem, such as tumors or nodes in the head and neck region. Therefore, approaches are needed to assist the radiation therapist in finding anatomical structures of interest using ultrasound.

SUMMARY OF THE INVENTION

The present invention provides methods and systems for assisting users in locating anatomical structures of interest using ultrasound imaging devices. One exemplary application of the invention is ultrasound-based IGRT.

In various aspects, a planning CT image and planning ultrasound image are acquired. For example, the planning ultrasound scan may have been taken in the CT room, where typically more time is available for scanning, and it is desirable to utilize these images in the treatment room (possibly on a daily or weekly basis), where the time and resources available to acquire ultrasound scans is limited. The user contours (e.g., draws, either programmatically or manually) the external body shape on the CT image, and in some cases the anatomical structure of interest may be displayed with the CT image, typically using the planning ultrasound or CT image, (the structure being referred to herein as the "scanning site contour" or SSC). For example, for breast patients, the SSC may correspond to a contour of the lumpectomy cavity within the breast. The path used to create the planning ultrasound image may be projected onto the contoured CT scan, resulting in an image of the desired ultrasound path on the CT scan. In some instances, the SSC may be included on the display, whereas in other instances it may not. The image can then be printed, or preferably, appear on a display in the treatment room, which the user may then consult while scanning the patient for subsequent ultrasound images. Because the path used to create the original ultrasound image is provided, the user does not need extensive training with regard to human anatomy or ultrasound scanning techniques, and the time required to obtain the image is greatly reduced. In addition, for breast scanning in radiation therapy for example, it is important not to apply probe pressure which would deform the breast during the scanning process, and by providing guidance as to where to place the probe, the operator can devote more attention to minimizing probe pressure.

In some instances, the planning CT is acquired, displayed and interrogated by the user prior to the planning ultrasound scan in order to aid in the localization of the organ of interest during the acquisition of the planning ultrasound. For example, the user can interrogate the CT image by scrolling through the planning CT data until the organ of interest comes into view, at which point the user has information about the organ's location relative to the landmarks on the surface of the planning CT, and can use these landmarks to guide acquisition of the planning ultrasound.

Where the SSC and external patient surface contour are contoured on the planning CT, but no planning ultrasound is available, the invention provides may facilitate the identification of the desired ultrasound scanning path using the two contours. In some cases, the desired path is found by tracing a line on the external contour which minimizes the distance between the line and the SSC. The path line may then be projected onto the external surface for visualization, as previously described. Such techniques may improve ultrasound scanning in both the treatment and planning rooms, and is especially useful in the planning room as there is no previous ultrasound image to use as a guide.

In some embodiments, the invention provides real-time feedback to the user as to the current probe position relative to the intended path. The three-dimensional location of the probe is known via a tracking system (such as a guided mechanical arm or optical-based tracking system), and this information can be overlaid with the current location of the probe relative to the external surface contour and intended path, indicating both where the probe is and where it should be.

BRIEF DESCRIPTION OF THE DRAWINGS

In the drawings, like reference characters generally refer to the same parts throughout the different views. Also, the drawings are not necessarily to scale, emphasis instead is generally being placed upon illustrating the principles of the invention.

DETAILED DESCRIPTION

Figure 1:
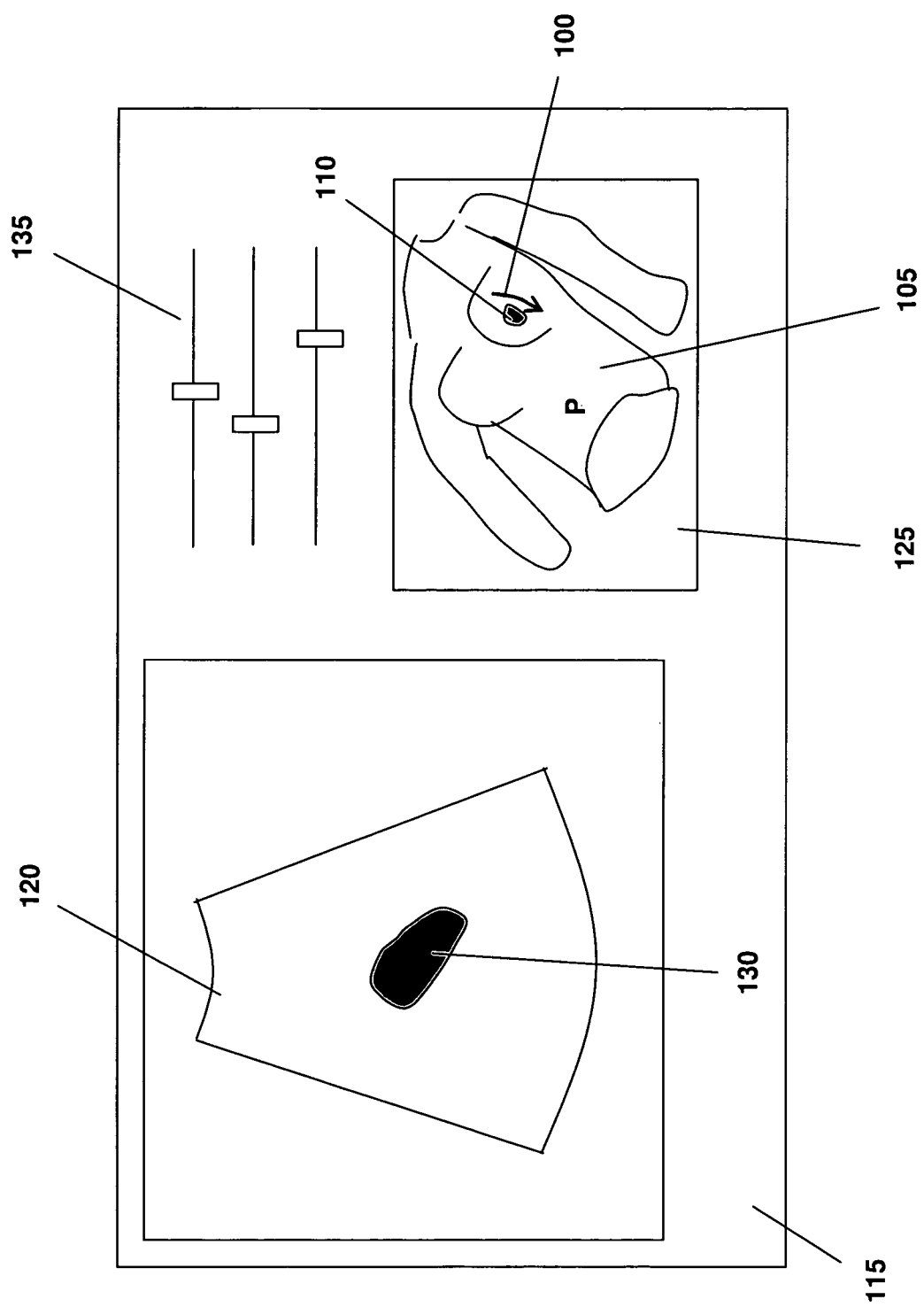
FIG. 1 illustrates one embodiment of a screen display indicating a proposed path and external contour surface for obtaining ultrasound images.

FIG. 1 illustrates one embodiment of the invention in which a path suggestion line 100 is shown projected onto an external contour 105 of a patient P. A scanning site contour (SSC) 110 is also shown, and may be derived from a three-dimensional surface contour of the anatomical structure of interest, in this case a breast lumpectomy site. In instances in which the SSC lies within the external contour, the contours may be displayed in semi-transparent fashion to allow full visibility of the SSC and other anatomical features. The three-dimensional information may be manipulated to improve viewing (using, for example, conventional visualization devices and/or software), including being be rotated and/or zoomed. The images may also be printed, but preferably are available directly on an ultrasound scanning screen 115 in a treatment planning and/or delivery room. In brief summary, an operator scans the patient using an ultrasound device while reviewing a real-time image 120 to find the area of interest. Using the location-guidance image 125, the operator can find the correct treatment delivery location, indicated in FIG. 1 at 130. The user can then adjust ultrasound settings 135, and obtain a three-dimensional scan which includes the intended treatment region by visually reproducing the intended scanning path 100 on the patient's skin.

In ultrasound-based IGRT, the ultrasound probe may be tracked (typically in real-time or near real-time) such that its three-dimensional position and orientation in space is known with respect to landmarks or other system components in the treatment room. In this fashion, the ultrasound slices can be positioned in space relative to the corresponding coordinates of the treatment room and/or a linear accelerator used to deliver radiotherapy. Techniques for tracking ultrasound devices typically rely on either a mechanical arm affixed to the probe or an optical camera attached to a fixed location in the room (often the ceiling) which tracks passive or active markers affixed to the probe.

Figure 2:
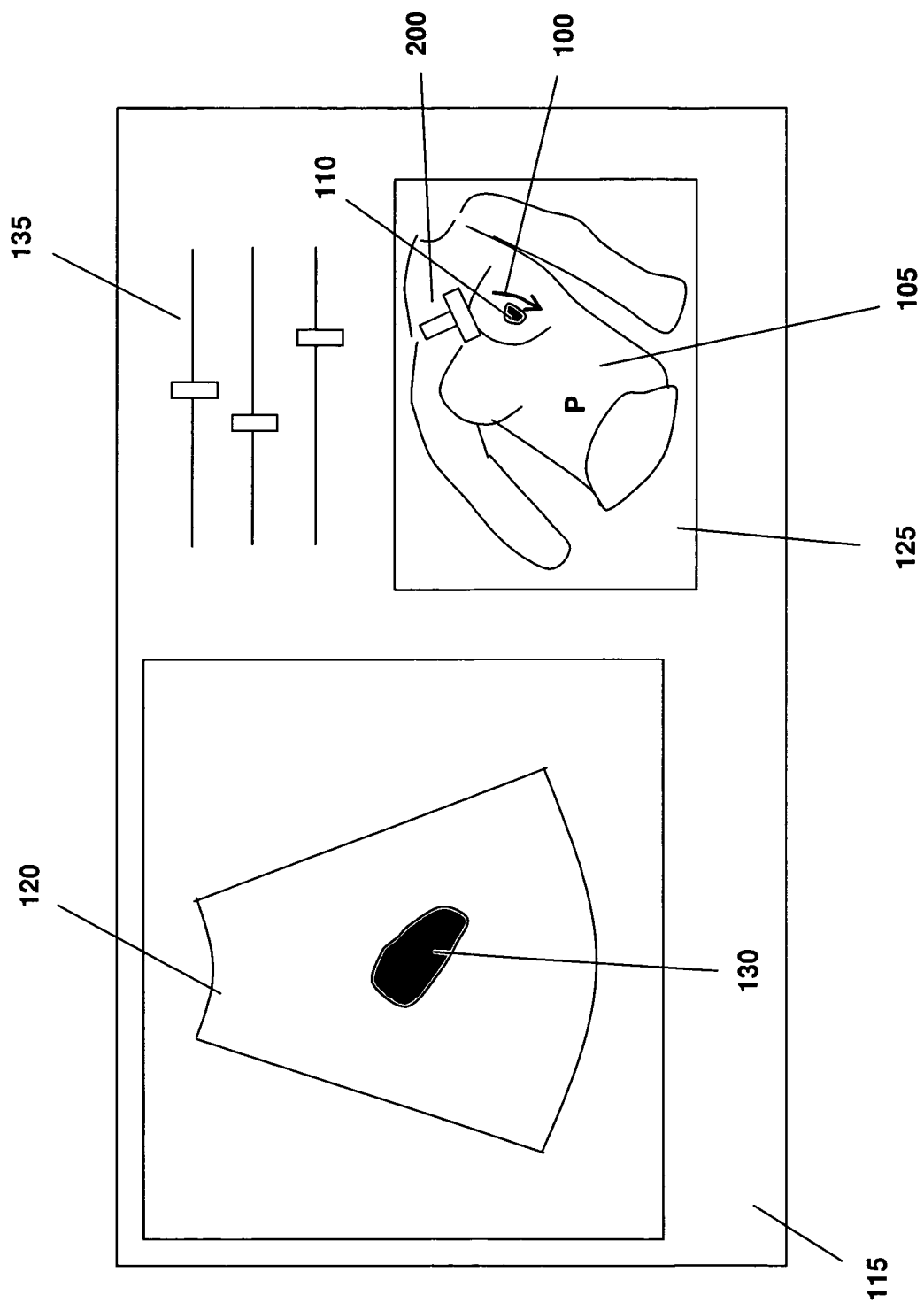
FIG. 2 illustrates the screen display of FIG. 1 with a current location of an ultrasound probe superimposed on the suggested scan path and external contour surface.

Referring to FIG. 2, a representation of the probe 200 (based on its location as determined above) is shown in the location-guidance image 125. The probe representation 200 may be updated in real-time as the operator moves the probe according to tracking information obtained from the tracking system, helping the operator see how close the current probe position is relative to the suggested path 100 (and thereby enabling the operator to include the appropriate anatomy in the scan with minimal searching). It also allows the operator to reproduce the same (or approximately the same) scan from one radiotherapy treatment session to the next.

Figure 3:
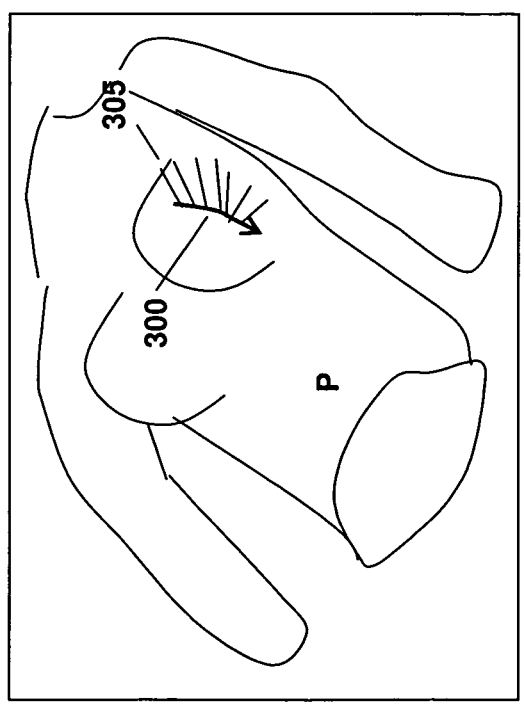
FIG. 3 illustrates one embodiment of a display indicating suggested probe angles along the suggested scan path of FIG. 1.

In some embodiments, the probe representation denotes both an angle and a position of the probe in space and relative to the patient P, while in some cases only its position is indicated. In certain variations, the intended scanning path 100 is shown as a line, while in others it also denotes a suggested direction of travel for the probe along the line. For example, in FIG. 3, the intended scanning path 300 includes a series of lines 305 perpendicular to the scanning path 100 indicating the intended scan direction along the path, thus indicating whether, for example, the path was scanned in a sweeping fashion or a translational motion. In some embodiments, a movie loop may be compiled showing an actual representation of the suggested probe motion along the intended scan path, indicating a more detailed version of the motion.

In some cases, a high-quality scan may have already been obtained in a first scanning session (typically during a treatment planning phase), and this scan may then be reproduced in future scanning sessions and used as a guide for augmenting the CT image with a preferred ultrasound path. In planning sessions, there is generally more time to obtain a good scan than in a treatment session, and the operators are typically more experienced and can obtain higher quality ultrasound scans than a radiotherapy technician who is not familiar with the representations of the anatomical structures in ultrasound images. In this case, the external contour 105 may be obtained from the CT and the SSC obtained from either the CT or the initial ultrasound image.

The external contour 105 can be drawn slice-by-slice on the CT scan, and converted into a three-dimensional surface (which can be represented as a mesh, for example) before being provided to the scanning system. In some cases, the three-dimensional surface is extracted automatically using techniques, such as thresholding, which uses differences in pixel characteristics find the interface between air and tissue. Similarly, the SSC can be found by either manually segmenting a region of interest in the CT or ultrasound image, or can be centered about a point in the general area of interest and defining the SSC as a sphere centered at that point.

In one embodiment, the suggested scanning path can be found by analyzing the temporal tracked probe positions of the first approved scan using, for example, the tracking data supplied by the tracking system and determining the position of a given pixel in the ultrasound image throughout the progression of the three-dimensional scan. In some implementations, the top-central pixel may be used as the reference pixel because it can be related to the center of the probe. The three-dimensional path of the reference pixel generates a series of three-dimensional points in space, which when connected in order define the scanning path. If the direction of the probe along the path is also of importance, this can be found by finding a vector connecting the top-center reference pixel and any other pixel in the center line of the ultrasound image. In general, if the CT and ultrasound image were acquired at nearly the same time with the patient in substantially the same position, the path will fall directly on the external contour. In some cases, if there are inaccuracies or if the patient moved or breathed during the scan, the path may not fall exactly on the skin. In some cases it may be preferable to project the path directly onto the external contour.

Figure 4:
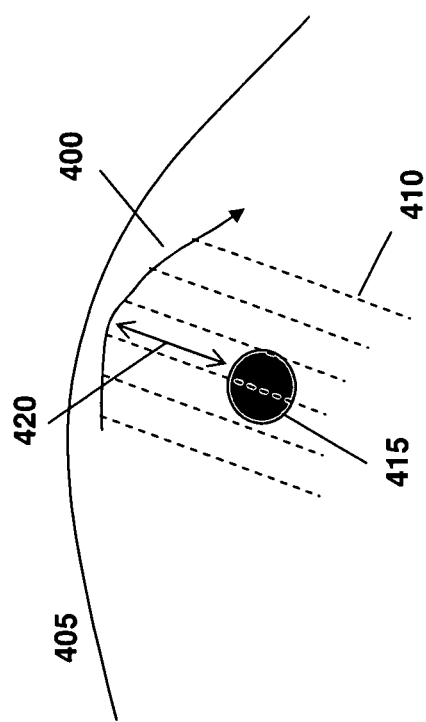
FIG. 4 illustrates one embodiment of the invention in which a suggested scan path is constructed without the benefit of a previously-obtained ultrasound scan.

In some applications, the invention facilitates the definition of a scanning path without the benefit of an initial ultrasound image. In such cases, the suggested scan path may be defined automatically using a previously acquired CT dataset with an associated external contour as input. Referring to FIG. 4, the suggested scan path 400 can be extracted by finding a path which is constrained to lie on the external contour 405, and for which perpendicular lines 410 pass through the SSC 415. In general there are many paths which will satisfy this condition, and therefore additional constraints may be imposed to determine the preferred path. For example, one such constraint is to minimize the distance 420 along each perpendicular line between the SSC and the surface. For example, the scan path may be calculated at the depth below the patient's skin of the SSC by finding an arbitrary line which passes through the SSC, and then projecting this line to the external contour surface such that the distance between the original line and the projected line is minimized. Continuity between the perpendicular lines should also be enforced since the ultrasound scan should be smooth. Further, the algorithm determines whether the preferred path is a sweeping, "fan" motion or a translational scan, in which all the perpendicular lines are substantially parallel to each other. Even with these constraints, there remains a number of possible paths, but in general choosing one such path is sufficient to guide the user.

Figure 5:
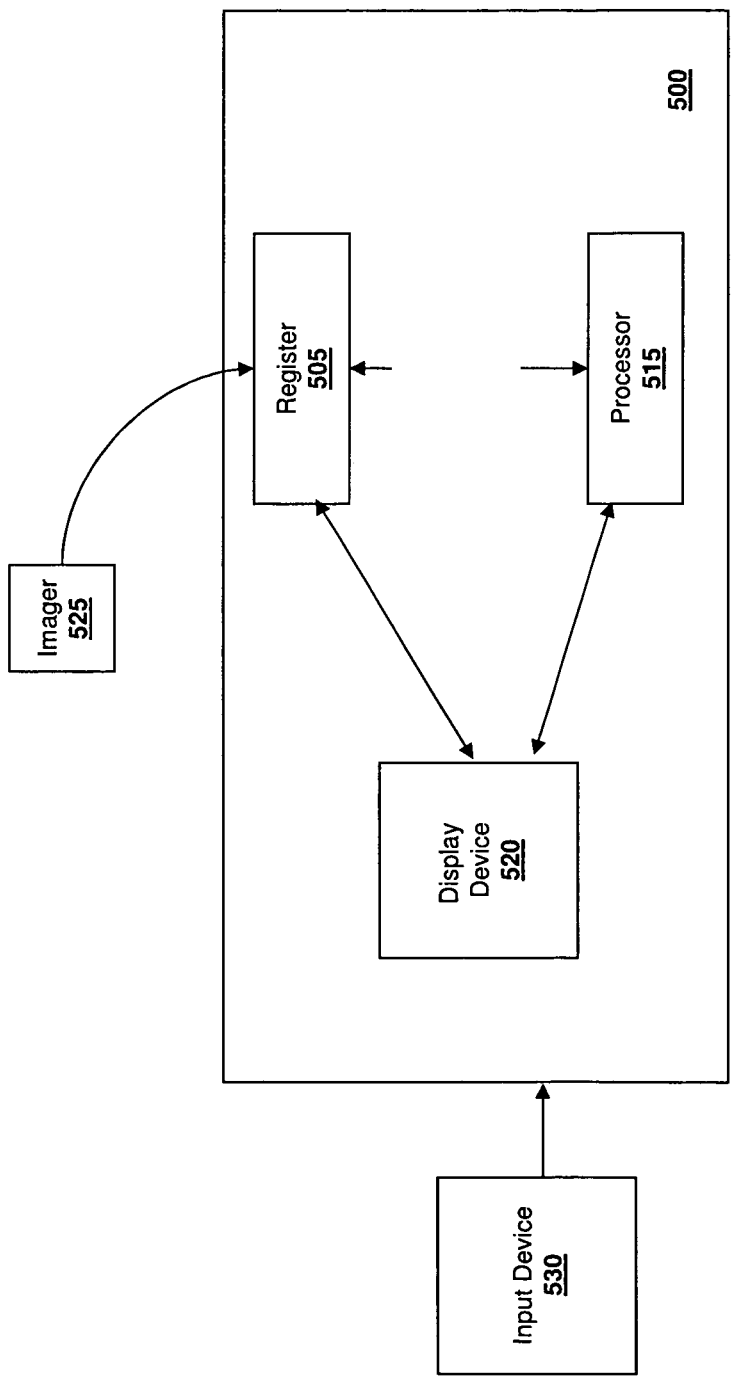
FIG. 5 is a schematic representation of a system in accordance with an embodiment of the invention.

FIG. 5 schematically depicts a hardware embodiment of the invention realized as a system 500 for presenting a preferred path for obtaining an ultrasound image. The system 500 comprises a register 505 and a processor 515.

The register 505, which may be any suitably organized data storage facility (e.g., partitions n RAM, etc.), receives images from an imager 525 such as an MRI, CT/PET scanner, ultrasound device, or x-ray device. In some embodiments, the images are stored on a data storage device separate from the imager (e.g., a database, microfiche, etc.) and sent to the system 500. The register 505 may receive the images through conventional data ports and may also include circuitry for receiving analog image data and analog-to-digital conversion circuitry for digitizing the image data.

The register 505 provides the image to the processor 515 which implements the functionality of the present invention in hardware or software, or a combination of both on a general-purpose computer. In addition, such a program may set aside portions of a computer's random access memory to provide control logic that affects one or more of the image capture, user manipulation (using, for example, an input device 530) and presentation on a display 520. In such an embodiment, the program may be written in any one of a number of high-level languages, such as FORTRAN, PASCAL, C, C++, C#, Java, Tel, or BASIC. Further, the program can be written in a script, macro, or functionality embedded in commercially available software, such as EXCEL or VISUAL BASIC. Additionally, the software can be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the art that various changes in form and detail may be made therein without departing from the spirit and scope of the invention as defined by the appended claims.

What is claimed is:

1. A method of presenting a suggested path for an ultrasound probe to travel along a surface of a patient, the method comprising:
    obtaining a three-dimensional image of the patient from an imaging device, the three-dimensional image including image data corresponding to an anatomical portion of the patient;
    defining, based on the three-dimensional image, a graphical representation of an external three-dimensional contour of the surface of the patient;
    determining the suggested path for the ultrasound probe to travel along the external three-dimensional contour of the surface of the patient; and
    generating, for presentation on a display, data that represents at least a portion of a previously acquired image of the anatomical portion and the suggested path in spatial relation along the external contour, wherein the suggested path includes a line displayed on the graphical representation of the external three-dimensional contour for the ultrasound probe to travel along and is configured to guide a movement of the ultrasound probe over the patient along the suggested path;
    tracking a position of the ultrasound probe during acquisition of the ultrasound image; and
    generating, for presentation on the display, data that represents a substantially real-time position of the ultrasound probe in spatial relation to the external contour and the suggested path.

2. The method of claim 1, further comprising:
    defining, based on the three-dimensional image, a scanning site contour that includes an area corresponding to the anatomical portion; and
    generating data to display the scanning site contour.

3. The method of claim 2, wherein determining the suggested path further includes constraining the suggested path to the external contour such that the desired ultrasound image reflects the area defined by the scanning site contour.

4. The method of claim 1, wherein the position of the ultrasound probe is determined using an optical tracking system.

5. The method of claim 1, wherein the position of the ultrasound probe is determined using a mechanical tracking system.

6. The method of claim 3, wherein constraining the suggested path to the external contour further comprises:

determining a first line passing through the scanning site contour in the three-dimensional image; and determining the suggested path by substantially minimizing a distance between the first line and a projection of the first line to the external contour of the patient.

7. The method of claim 6, wherein the first line is defined under the patient's skin, and wherein the method further comprises determining the suggested path base on the projection of the first line to the external contour of the patient.

8. The method of claim 1, further comprising:

acquiring the previously acquired image;

tracking a series of positions of the ultrasound probe during the acquisition of the previously acquired image; and determining the suggested path based on the series of positions of the ultrasound probe during the acquisition of the previously acquired image, wherein the desired ultrasound image is a substantial reproduction of the previously acquired image.

9. A method of presenting a suggested path for an ultrasound probe to travel along an external surface of a patient, the method comprising:

obtaining an external three-dimensional surface representation of the patient;

determining the suggested path for the ultrasound probe to travel along the external three-dimensional surface representation of the patient based at least in part on a prior scan including a plurality of previously acquired ultrasound images of the anatomical portion; and generating, for presentation on a display, data that represents at least a portion of a previously acquired ultrasound image of the anatomical portion and the surface representation in spatial relation along the suggested path, the suggested path defining a line displayed on the surface representation for the ultrasound probe to travel along, wherein the data is configured to guide a movement of the ultrasound probe along the suggested path;

tracking a position of the ultrasound probe during acquisition of the ultrasound image; and generating, for presentation on the display, data that represents a substantially real-time position of the ultrasound probe in spatial relation to the external contour and the suggested path.

10. The method of claim 9, further comprising obtaining the surface representation from a non-ultrasound image.

11. The method of claim 9, further comprising tracking the ultrasound probe during a subsequent ultrasound scan.

12. A system for presenting a suggested path for an ultrasound probe to travel along a surface of a patient, the system comprising:

a register for storing a three-dimensional image of the patient, the three-dimensional image including image data corresponding to an anatomical portion of the patient; and a processor configured to:

define, based on the three-dimensional image, a graphical representation of an external three-dimensional contour of the surface of the patient that reproduces at least a portion of a previously acquired image of the anatomical portion;

determine the suggested path for the ultrasound probe to travel along the external three-dimensional contour of the surface of the patient; and generate, for presentation on a display, data that represents at least a portion of a previously acquired image of the anatomical portion and the suggested path in spatial relation along the external three-dimensional contour, wherein the suggested path includes a line displayed on the graphical representation of the external contour for the ultrasound probe to travel along along the suggested path;

receive, from a tracking system, tracking data representing a position of the ultrasound probe during acquisition of the ultrasound image; and generate, for presentation on the display, data that represents a substantially real-time position of the ultrasound probe in spatial relation to the external contour and the suggested path.

13. The system of claim 12, wherein the processor is configured to define, based on the three-dimensional image, a scanning site contour that includes an area corresponding to the anatomical portion and generate data to display the scanning site contour.

14. The system of claim 13, wherein the processor is configured to determine the suggested path by constraining the suggested path to the external contour such that the desired ultrasound image reflects the area defined by the scanning site contour.

15. The system of claim 12, wherein the position of the ultrasound probe is determined using an optical tracking system.

16. The method of claim 12, wherein the position of the ultrasound probe is determined using a mechanical tracking system.

* * * * *

UNITED STATES PATENT AND TRADEMARK OFFICE
CERTIFICATE OF CORRECTION

| | |
|---|---|
| PATENT NO. | : 10,531,858 B2 |
| APPLICATION NO. | : 12/176774 |
| DATED | : January 14, 2020 |
| INVENTOR(S) | : Lachaine et al. |

Page 1 of 1

It is certified that error appears in the above-identified patent and that said Letters Patent is hereby corrected as shown below:

On the Title Page

In item (57), in "Abstract", in Column 2, Line 5, delete "within the within the" and insert --within the-- therefor In the Claims In Column 8, Line 23, in Claim 12, delete "along along" and insert --along-- therefor Signed and Sealed this
Eighteenth Day of August, 2020

Andrei Iancu
*Director of the United States Patent and Trademark Office*